United States Patent [19]

Orzalesi et al.

[11] 4,061,668
[45] Dec. 6, 1977

[54] PROCESS FOR THE PREPARATION OF 2-(4-ISOBUTYLPHENYL)-PROPIOHYDROXAMIC ACID

[75] Inventors: Giovanni Orzalesi; Renato Selleri, both of Florence, Italy

[73] Assignee: Societa Italo-Britannica L. Manetti - H. Roberts & C., Florence, Italy

[21] Appl. No.: 733,942

[22] Filed: Oct. 19, 1976

Related U.S. Application Data

[63] Continuation of Ser. No. 573,056, April 30, 1975, abandoned.

[30] Foreign Application Priority Data

Dec. 6, 1974    Italy .................................. 54400/74

[51] Int. Cl.$^2$ .............................................. C07C 83/10
[52] U.S. Cl. ................................................. 260/500.5 H
[58] Field of Search ................................ 260/500.5H

[56] References Cited

U.S. PATENT DOCUMENTS

| 2,346,665 | 4/1944 | Cupery | 260/500.5 H |
| 2,943,092 | 6/1960 | Smrt et al. | 260/500.5 H |
| 3,479,396 | 11/1969 | Buu-Hoi et al. | 260/500.5 H |
| 3,641,123 | 2/1972 | Hayman et al. | 260/500.5 H |
| 3,819,702 | 6/1974 | Lafon | 260/500.5 H |

Primary Examiner—Joseph E. Evans

[57] ABSTRACT 2-(4-Isobutylphenyl)-propiohydroxamic acid is prepared by mixing anhydrous methanol with 2-(4-isobutylphenyl)-propionitrile, saturating the mixture with dry hydrogen chloride, reacting, diluting the reaction product with ethyl ether, reacting the precipitate with hydroxylamine hydrochloride in methanol and with 50% NaOH, stirring, diluting with water and precipitating with carbon dioxide.

1 Claim, No Drawings

PROCESS FOR THE PREPARATION OF 2-(4-ISOBUTYLPHENYL)-PROPIOHYDROXAMIC ACID

This is a continuation of application Ser. No. 573,056, filed Apr. 30, 1975, now abandoned.

The object of the invention is a new process for the preparation of 2-(4-isobutylphenyl)-propiohydroxamic acid. In the patent application Ser. No. 428,835, now abandoned a new chemical compound 2-(4-isobutylphenyl)-propiohydroxamic acid is described, corresponding to the formula $C_{13}H_{19}NO_2$, which is represented by the following structure:

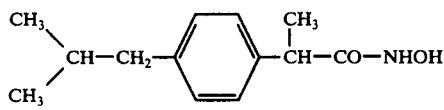

Its molecular weight is 221.3.
Centesimal elementary analysis of the compound:
C 70.55 (found 70.11)
H 8.65 (found 9.02)
N 6.33 (found 6.15)
O 14.46 (by difference)

One process described in the above application for the preparation of the compound is the following:

2.3 g of 2-(4-isobutylphenyl)-propionic acid — a compound which is well known and described in chemical literature — are solved in absolute ethanol, and 0.5 ml concentrated sulphuric acid is added thereafter. The whole is reflux heated for 4 hours and the reaction mixture is concentrated under reduced pressure. An oily residue is obtained which is cold treated with a saturated aqueous $NaHCO_3$ solution until its effervescence has disappeared. This latter treatment is preformed by small successive additions. The obtained solution is extracted three times, each time with 50 ml ethyl ether. The etheric extracts are added together, dried on $MgSO_4$ and evaporated. Thus an oily residue is obtained which weighs approximately 2.1 g and consists of the ethyl ester of the starting acid. This ester is used such as it is in the further process.

To a solution of sodium methylate consisting of 0.5 g Na in 15 ml anhydrous methanol there is added a solution of 0.7 g hydroxylamine hydrochlorate in 10 ml anhydrous methanol. It is filtered from the precipitated NaCl and to this mixture the previously prepared 2.1 g of ethyl ester is added. The whole is reflux heated for 15 minutes, cooled, slightly acidified with a 20% HCl solution, washed with water and finally with petroleum ether; it is crystallized from acetone/petroleum ether, to yield approximately 1 g of the desired product. As already stated, it appears in the shape of white, shiny laminar scales, and has a melting point of 119°-121° C on Kofler's hot stage.

A second process described in the above application for the synthesis of the compound is the following:

Adding, under stirring and cooling, a solution of potassium hydroxide in methanol to a solution of hydroxylamine hydrochlorate in methanol and precipitating the potassium chloride; adding to said mixture, under continued stirring and cooling, an ethyl ether solution of 2-(4-isobutylphenyl)-propionic acid; suction filtering this mixture and washing the residue with methanol; putting together the methanol used for the washing and the filtrate and evaporating the whole at a reduced pressure; acidifying the resulting concentrated solution, letting it stand, suction filtering it; taking up the residue in petroleum ether and filtering again, thus obtaining the desired acid.

Object of the present invention is a new process for the preparation of 2-(4-isobutylphenyl)-propiohydroxamic acid. This process has the advantage over those disclosed in the previous application that instead of starting from a propionic acid derivative and isolating the well known intermediate compounds having an ester or carboxylic group, a starting compound containing a cyano group is used, which is converted into the hydroxamic acid compound by reaction with hydrochloric acid, precipitation and treatment with hydroxylamine hydrochloride.

The process of the invention comprises the steps of preparing a solution by mixing anhydrous methanol to 2-(4-isobutylphenyl)-propionitrile, saturating said mixture with dry hydrochloric acid gas, reacting and diluting the reaction product with ethyl ether, reacting the precipitate with hydroxylamine hydrochloride in a methanol medium and with a 50% sodium hydroxide solution, stirring and at the end of the reaction diluting with water and precipitating by means of carbon dioxide to obtain the desired compound as a precipitate.

The invention is more fully described in the following example given for a purely illustrative and in no way limitative purpose.

EXAMPLE

In an airtight reactor provided with a stirrer, there were charged:
2-(4-isobutylphenyl)-propionitrile: 186 g (1 mole)
anhydrous methanol: 200 ml (5 moles)
(mole ratio 1:5).

The mixture was saturated with dry HCl gas, while cooling it to about 0° C.

The reactor was sealed and stirring was kept up for 120 hours at room temperature.

Thereafter the mixture was diluted with 700 ml dry ethyl ether, thus giving rise to a precipitate. This precipitate, collected and separated by suction filtering, was placed into an airtight reactor provided with a stirrer together with 139 g (2 moles) hydroxylamine hydrochloride (mole ratio 1:2) and 600 ml methanol.

240 ml of an aqueous 50% w/w sodium hydroxide solution was added under stirring (volume ratio of methanol to aqueous sodium hydroxide 2.5:1) while cooling the reactor to maintain the reaction temperature at about 10° C. Reaction was brought about in 48 hours under stirring followed by diluting with 5 volumes $H_2O$, then acidifying by $CO_2$.

As a result of this process, 2-(4-isobutylphenyl)-propiohydroxamic acid was precipitated and separated by suction filtration. The obtained product could be purified by crystallization. It melted at 119°-121° C on Kofler's hot stage.

What is claimed is:
1. A process for the preparation of 2-(4isobutylphenyl)-propiohydroxamic acid comprising the steps of forming a mixture of 2-(4-isobutylphenyl)-propionitrile as a starting compound and anhydrous methanol, saturating said mixture with dry hydrochloric gas under cooling, reacting and then diluting the reaction product by ethyl ether, whereby a precipitate is formed, reacting the precipitate with a mixture of a methanol solution of hydroxylamine hydrochloride and a sodium hydroxide solution under stirring, diluting the reaction product with water and precipitating the desired compound by carbon dioxide.

* * * * *